United States Patent [19]

Tachibana et al.

[11] Patent Number: 5,961,919
[45] Date of Patent: Oct. 5, 1999

[54] DEODORIZING AND STERILIZING DEVICE HAVING CATALYST DETERIORATION SENSING FUNCTION

[75] Inventors: Hirokazu Tachibana, Hirakata; Akiyoshi Hattori, Yawata; Nobuyuki Yoshiike, Ikoma; Akihiko Yoshida, Hirakata, all of Japan

[73] Assignee: Matsushita Electric Industrial Co., Ltd., Osaka, Japan

[21] Appl. No.: 08/981,823

[22] PCT Filed: May 13, 1997

[86] PCT No.: PCT/JP97/01607

§ 371 Date: Mar. 12, 1998

§ 102(e) Date: Mar. 12, 1998

[87] PCT Pub. No.: WO97/42981

PCT Pub. Date: Nov. 20, 1997

[30] Foreign Application Priority Data

May 15, 1996 [JP] Japan .................................. 8-120366

[51] Int. Cl.[6] ...................................................... A61L 2/14
[52] U.S. Cl. ........................ 422/3; 422/4; 422/5; 422/22; 422/105; 422/116; 422/121; 422/186.07; 422/306; 422/900; 95/3; 95/8; 96/417; 96/419; 96/424
[58] Field of Search ................... 422/2, 3, 4, 5, 422/22, 105, 116, 120, 121, 186, 186.04, 186.07, 306, 900; 95/3, 8; 96/417, 419, 424

[56] References Cited

U.S. PATENT DOCUMENTS

| | | |
|---|---|---|
| 4,343,765 | 8/1982 | Elston et al. .............................. 422/3 |
| 5,034,367 | 7/1991 | Falke et al. .............................. 502/159 |
| 5,681,533 | 10/1997 | Hiromi .................................... 422/121 |
| 5,752,878 | 5/1998 | Balkany ............................. 422/186.07 |
| 5,788,930 | 8/1998 | McMurray .............................. 422/121 |

FOREIGN PATENT DOCUMENTS

| | | |
|---|---|---|
| 3-267748 | 11/1991 | Japan . |
| 4-138167 | 5/1992 | Japan . |
| 6-262098 | 9/1994 | Japan . |
| 7-299128 | 11/1995 | Japan . |
| 9-075436 | 3/1997 | Japan . |

Primary Examiner—Terrence R. Till
Assistant Examiner—Fariborz Moazzam
Attorney, Agent, or Firm—McDermott, Will & Emery

[57] ABSTRACT

A deodorizing and disinfecting apparatus having catalyst deterioration detection function of the present invention comprises: an air supply portion for inhaling air inside; an ozone generating portion for discharging ozone to the inhaled air: a catalyst for accelerating deodorizing and disinfecting actions and decomposition of the ozone disposed downstream from the ozone generating portion; an ozone sensor for detecting the concentration of remaining ozone disposed downstream from the catalyst; and means for repeating a cycle including stop of ozone discharge from the ozone generating portion for a predetermined time period when the concentration of the remaining ozone reaches a predetermined concentration or more, and for determining that the catalyst is deteriorated when a condition wherein an interval between times when the concentration of the remaining ozone is not less than a predetermined concentration becomes shorter than a predetermined time period is recognized at a predetermined frequency, and then for stopping discharge of the ozone.

7 Claims, 3 Drawing Sheets

DEODORIZING AND STERILIZING DEVICE HAVING CATALYST DETERIORATION SENSING FUNCTION

TECHNICAL FIELD

The present invention relates to a deodorizing and disinfecting apparatus using ozone.

BACKGROUND ART

Since ozone exhibits a strong oxidizing action, it has been used in many fields such as water treatment, medical and food industries in recent years, in order to perform deodorization, disinfection and the like. Lately, attention has been paid to ozone for use in various countermeasures for odors in living spaces, and many apparatuses using ozone have been developed.

As described above, ozone exhibits such useful action. However, ozone itself has special odor. Therefore, when ozone is used for an apparatus, it is necessary to prevent ozone from being discharged to the outside of the apparatus. For this reason, ozone remaining after treatment is subjected to a thermal decomposition method or a decomposition method with a catalyst. Among these methods, the method with the catalyst is relatively simple, and thus generally used. However, in the method of decomposing ozone by using the catalyst, there is apprehension that the activity of the catalyst lowers gradually, and ozone in an excessive concentration is discharged to the outside of the apparatus after use for a long period of time or because of changes in environmental conditions or the like.

DISCLOSURE OF INVENTION

An object of the present invention is to provide a highly reliable deodorizing and disinfecting apparatus capable of preventing a discharge of remaining ozone to the outside of the apparatus even when the catalyst is deteriorated.

The present invention provides an ozone deodorizing and disinfecting apparatus comprising an ozone generating portion, a catalyst having functions for accelerating ozone deodorizing and disinfecting actions and for decomposing the ozone, an ozone sensor and an air supply portion, and additionally having functions for repeating a cycle including temporary stop of ozone discharge when the concentration of ozone remaining after treatment by the catalyst reaches a predetermined concentration or more and resumption of ozone discharge after an elapse of a predetermined time period, and then for determining that the catalyst has been deteriorated when a tendency wherein an interval between times when the concentration of the remaining ozone reaches a predetermined concentration becomes shorter than a predetermined time period is recognized at a predetermined frequency.

The deodorizing and disinfecting apparatus having the catalyst deterioration detection function of the present invention comprises: an air supply portion for inhaling air inside; an ozone generating portion for discharging ozone to the inhaled air; a catalyst for accelerating the deodorizing and disinfecting actions and for decomposition of ozone, disposed downstream from the ozone generating portion; and an ozone sensor for detecting the concentration of remaining ozone, disposed downstream from the catalyst; and further comprising means for repeating a cycle including stop of ozone discharge from the ozone generating portion for a predetermined time period when the ozone sensor detects that the concentration of the remaining ozone is not less than a predetermined concentration, and for determining that the catalyst has been deteriorated when a condition wherein an interval between times when the concentration of the remaining ozone in the continuous cycles is not less than a predetermined concentration becomes shorter than a predetermined time period is recognized at a predetermined frequency thereby stopping ozone discharge.

Furthermore, it is preferable that the apparatus further comprises alarm means for notifying that the catalyst has been deteriorated when the catalyst is determined to be deteriorated and ozone discharge is stopped. By this means, the user can be accurately notified of the need for replacement of the catalyst by indication, alarm sound or the like.

BEST MODE FOR CARRYING OUT THE INVENTION

Figure 1:
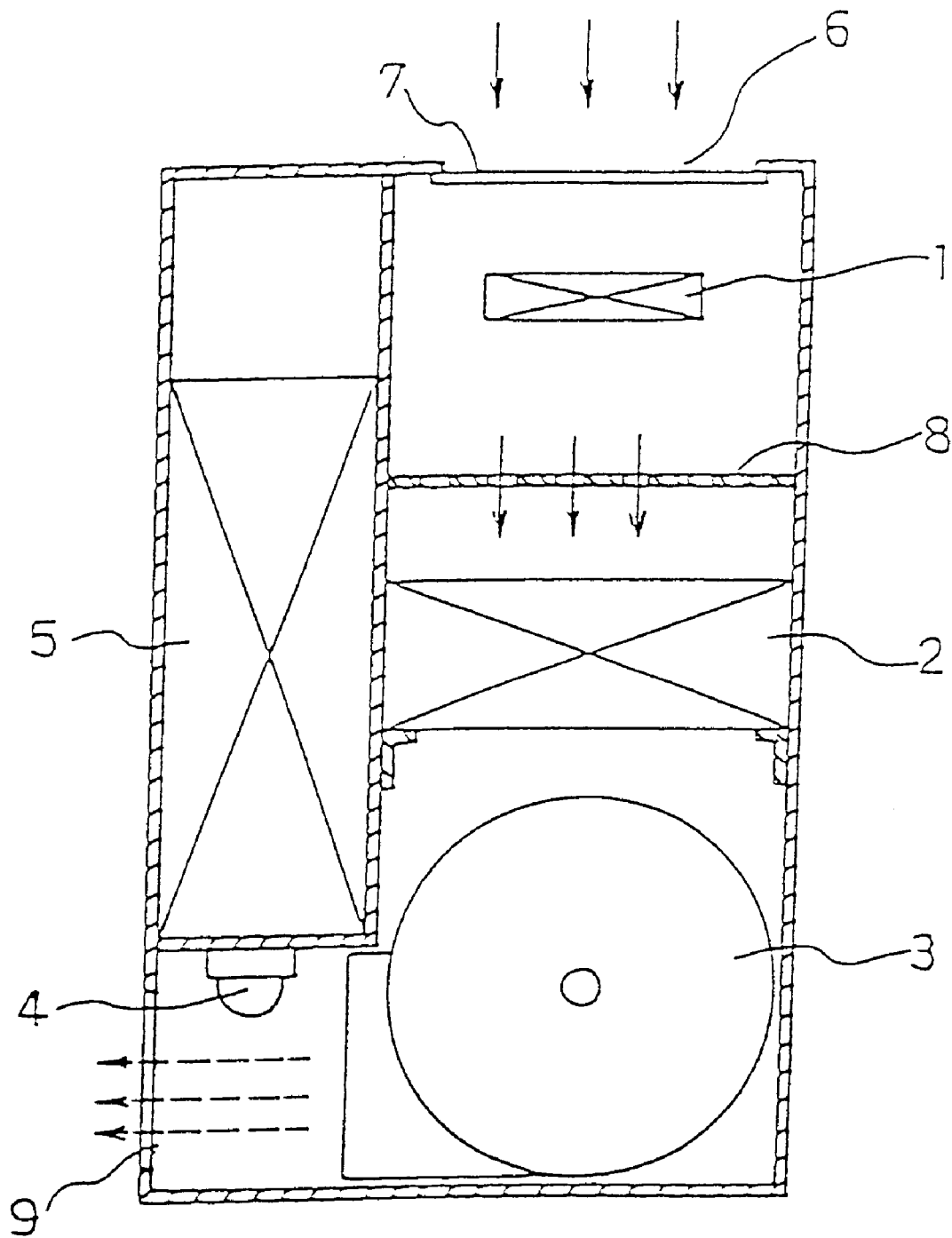
FIG. 1 is a sectional schematic view showing a deodorizing and disinfecting apparatus in accordance with an embodiment of the present invention.

Embodiments of the present invention will be detailed below referring to the drawings.

The basic structure of the deodorizing and disinfecting apparatus having the catalyst deterioration detection function in accordance with the present embodiment is shown in FIG. 1.

Air outside the apparatus is inhaled into the apparatus from an air suction port 6 by a fan 3. At this time, by a filter 7 disposed at the air suction port 6, dirt, dust and the like included in the influent air are removed. Next, a predetermined amount of ozone generated by an ozone generator 1 is delivered to the air. The air and the ozone are mixed nearly uniformly by a diffusion plate 8. Then, by mixing with the ozone, contaminants such as odor components and bacteria in the air are decomposed and removed. In addition, the air mixed with the ozone makes contact with a catalyst 2, whereby the actions of the ozone for decomposing and removing the contaminants are accelerated, and decomposition of the remaining ozone is also accelerated.

After the air inhaled into the apparatus is thus subjected to deodorizing and disinfecting treatment and cleaned, it is discharged from a clean air discharge port 9 to the outside of the apparatus.

Upstream from the clean air discharge port 9, an ozone sensor 4 is disposed to detect the concentration of the remaining ozone in the clean air. The ozone sensor 4 delivers a signal corresponding to the detected concentration of the remaining ozone to a signal processing portion 5.

Figure 2:
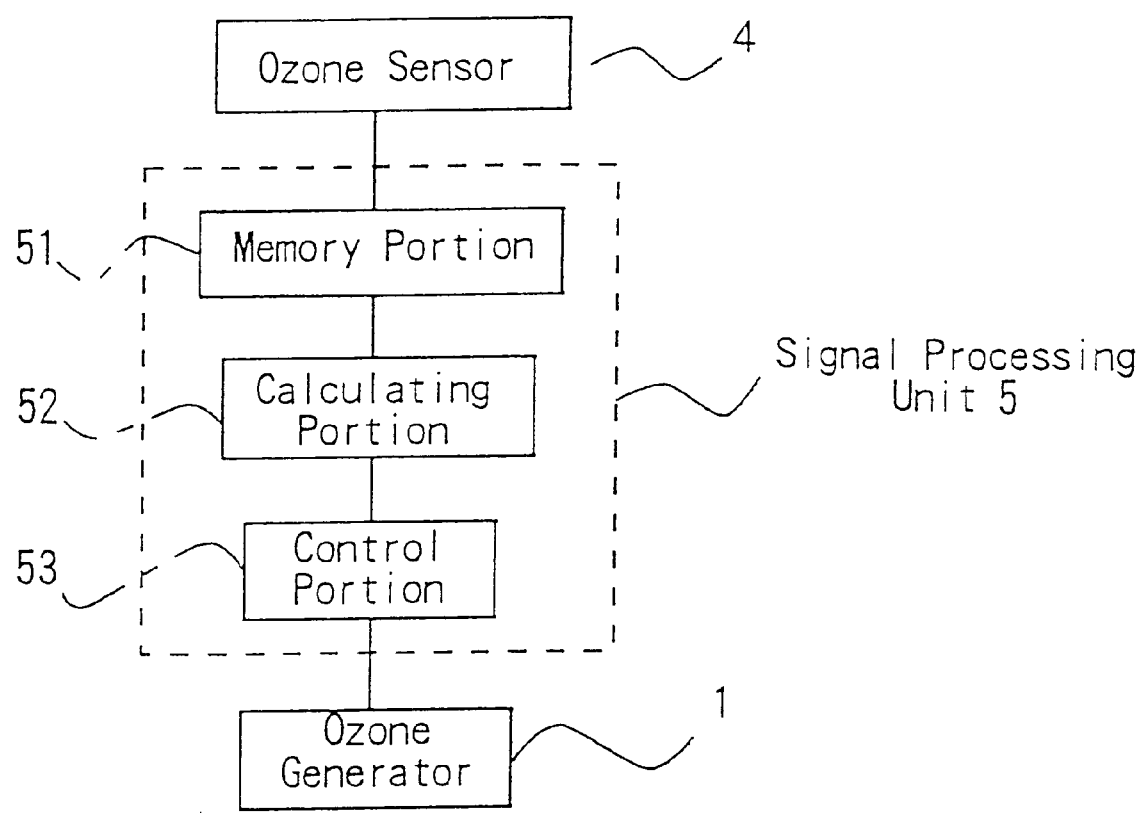
FIG. 2 is a block diagram showing a catalyst deterioration determination system of the same apparatus.

The signal processing portion 5 is provided with a memory portion 51, a calculating portion 52 and a control portion 53 as shown in FIG. 2.

In the memory portion 51, the allowable upper limit concentration of the remaining ozone, a time period required when the air downstream from the catalyst 2 in a condition including no ozone reaches the allowable upper limit ozone concentration while the catalyst 2 functions properly (hereinafter, referred to as a standard detection interval), and a standard detection time period for determining that the catalyst is deteriorated have been stored.

The calculating portion 52 compares the concentration of the remaining ozone on the basis of the output signal of the ozone sensor 4 with the allowable upper limit concentration thereby to determine whether the concentration is less than the allowable upper limit concentration or not. At this time, if the calculating portion 52 determines that the concentration of the remaining ozone is not less than the allowable upper limit concentration, it delivers a signal for temporarily stopping ozone discharge by the ozone generator 1 for a predetermined time period to the control portion 53. Therefore, the concentration of the remaining ozone decreases temporarily. However, when ozone discharge by the ozone generator 1 is resumed, the concentration of the remaining ozone increases and exceeds the allowable upper limit concentration again. The calculating portion 52 thus measures a time period after determining that the concentration of the remaining ozone was not less than the allowable upper limit concentration until the concentration of the remaining ozone is determined to be not less than the allowable upper limit concentration again (hereinafter referred to as a detection interval). When the detection interval becomes not more than the standard detection interval, the calculating portion 52 counts the number of the times, and compares it with the preset standard detection times. When the number of the times reaches the standard detection times, the calculating portion 52 determines that the catalyst 2 has been deteriorated and delivers a signal for stopping ozone discharge by the ozone generator 1 to the control portion 53.

In accordance with the signal from the calculating portion 52, the control portion 53 controls the ozone generator 1, and also controls a signal for indication, alarm or the like.

If the detection interval is longer than the standard detection interval, the activity of the catalyst 2 is determined to be normal, and the same cycle is repeated. The air deodorizing and disinfecting treatment thus continues. However, if the detection interval is shorter than the standard detection interval, and if a similar tendency is recognized a predetermined number of times, the catalyst 2 is determined to be deteriorated, and ozone discharge by the ozone generator 1 is stopped. The standard detection interval is set in consideration of the amount of ozone discharged by the ozone generator 1, a time period for temporarily stopping discharge, and the like. In addition, although it is not shown, deterioration of the catalyst is notified by an indication or an alarm sound.

Embodiment 1

In the present embodiment, the examinations described below were conducted by using a deodorizing and disinfecting apparatus having a catalyst deterioration detection function, which is similar to the above-mentioned apparatus.

The ozone generator 1 is provided with creepage discharge type ozone generating electrodes comprising an induction electrode and a discharge electrode formed on an alumina substrate, which generates ozone by so-called silent discharge. A thin-film sensing element mainly comprising a composite oxide containing $In_2O_3$ and $SnO_2$ at a molar ratio of Sn/(In+Sn)=3/100 was used as the ozone sensor 4. The catalyst 2 has a shape of honeycomb having a volume of about 100 $cm^3$, and is made of a metal oxide mainly comprising Mn.

As setting conditions, the allowable upper limit concentration of the remaining ozone was set at 0.05 ppm, the standard detection interval between two continuous times was set at 3 minutes, and a temporary ozone stopping time period was set at 30 seconds. Furthermore, when the detection interval became shorter than the above-mentioned standard detection interval five times continuously, the catalyst 2 was determined to be deteriorated.

Figure 3:
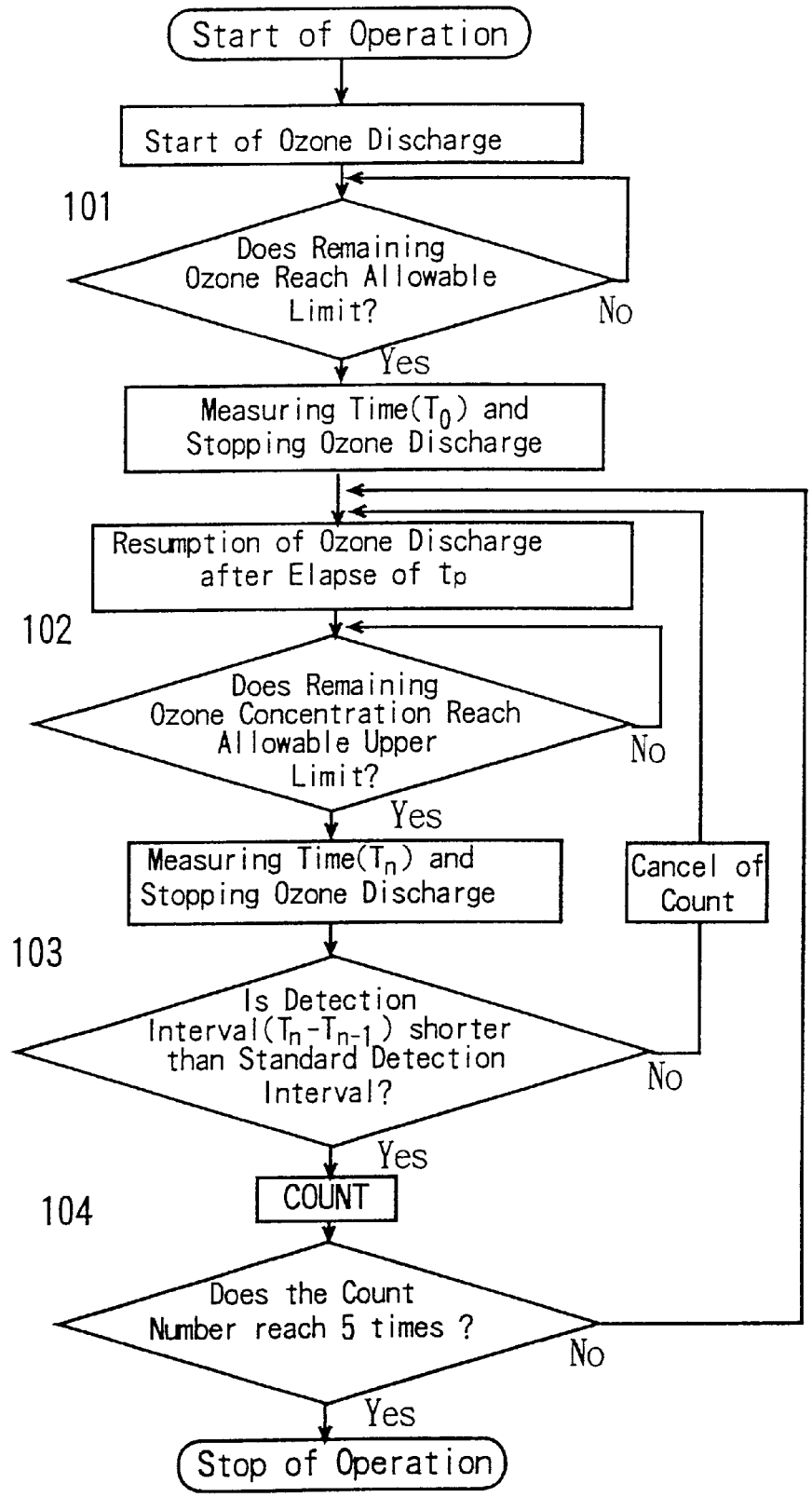
FIG. 3 is a flowchart showing a configuration of the signal processing portion of the apparatus.

Referring to the flowchart shown in FIG. 3, the catalyst deterioration detection function of the deodorizing and disinfecting apparatus in accordance with the present embodiment is described below.

When the apparatus is operated, the fan 3 starts suction, and the ozone generator 1 starts ozone discharge. The ozone sensor 4 detects ozone continuously during the operation of the apparatus. At step 101, if the activity of the catalyst 2 is lowered, and the concentration of the remaining ozone is determined to be reached the allowable upper limit concentration (0.05 ppm), the signal processing portion 5 measures time $T_o$ used as a start point. At the same time, the signal processing portion 5 delivers a signal for temporarily stopping ozone discharge to the ozone generator 1. By this signal, the concentration of the remaining ozone is lowered temporarily. After a lapse of predetermined time period $t_p$ (30 seconds) from the stop of ozone discharge, ozone discharge is resumed.

Next, at step 102, when the concentration of the remaining ozone becomes not less than the allowable upper limit concentration again, time $T_1$ is measured, and a detection interval $(T_1-T_o)$ is calculated. In addition, at the same time, ozone discharge is stopped. Then, the same cycle of resuming ozone discharge and calculating the detection interval $(T_n-T_{n-1}$: n is the number of cycles) when the concentration of the remaining ozone reaches the allowable upper limit concentration in the same way is repeated. At step 103, the number of times wherein the detection intervals are determined continuously to have been shorter than the standard detection interval (3 minutes) is counted.

If the detection interval is determined to have been not less than the standard detection interval before the count number reaches five, the count number is canceled once, ozone discharge is resumed after a lapse of $t_p$, and the same cycle for calculating the detection interval is repeated.

At step 104, when the count number reaches five, that is, when the detection interval becomes shorter than the standard detection interval five times continuously, the signal processing portion 5 delivers a signal for stopping ozone discharge to the ozone generator 1, and the apparatus stops.

The operation of the apparatus with conditions being set as described above was confirmed.

After a space having a volume sufficiently larger than the volume of the apparatus (about 1000 times as large as the volume of the apparatus) was filled with clean air, and the apparatus having been set in the above-mentioned conditions was installed in the space, and the space was hermetically sealed. Next, the fan 3 was operated, and the air outside the apparatus was inhaled at a flow rate of 7 liters/minute. In addition, ozone was generated and discharged by the ozone generator 1 so that the ozone concentration in the air was about 0.06 ppm, exceeding the decomposition capability of the catalyst 2. However, the ozone to be discharged from the clean air discharge port 9 to the outside of the apparatus was discharged to the outside the hermetically sealed space so as not to be inhaled again into the apparatus.

The detection interval, which was about 7 minutes immediately after the start, became shorter gradually, and became 2.5 minutes at the 30th cycle, shorter than the standard detection interval of 3 minutes. After this, the detection interval became about 2 minutes, and a cycle having a detection interval shorter than the standard detection interval was repeated five times. At this time, ozone discharge was stopped.

In this way, it is confirmed that the present apparatus operates properly.

Embodiment 2

In the present embodiment, a case of newly added conditions to improve the accuracy of catalyst deterioration detection in addition to the same conditions as those for embodiment 1 is described.

In the present embodiment, by using the same apparatus as that for embodiment 1, in addition to the same determination conditions as those for embodiment 1, it was also determined that deterioration has occurred in the case when a cycle having a detection interval shorter than the standard detection interval of 3 minutes was recognized 4 times or more while detection cycles were repeated 6 times. According to this method, improper determination can be prevented even in the case that the catalyst should be determined to be deteriorated essentially but the detection interval becomes longer than the standard detection interval because of some factors such as decrease in the amount of ozone, change in fan capability and the like.

In the present embodiment, first, the concentration of ozone discharged by the ozone generator was set at 0.06 ppm. In addition to this, when a cycle wherein the detection interval became shorter than the standard detection interval continued 3 times, the concentration of the discharged ozone was set at 0.03 ppm by adjusting the ozone generator. At this time, the detection interval became about 3.5 minutes. After an elapse of about 5 minutes, when the concentration of the discharged ozone was returned to its initial condition, the next detection interval became less than 3 minutes. In this way, at a stage wherein detection intervals less than 3 minutes were recognized in six detection cycles in total, the catalyst was determined to be deteriorated, and ozone discharge was stopped.

The present apparatus was operated continuously in actual living environments and its function was confirmed.

The present apparatus was installed in a living room having a volume of about 50 m$^3$, and operated continuously; as a result, after an elapse of about 2500 hours, the catalyst was determined to be deteriorated, and ozone discharge was stopped. At this time, the catalyst was taken out of the apparatus. When the ozone decomposition activity of the catalyst was measured, it was found that the activity was lowered to about 55% of its initial activity.

The ozone generator, the ozone sensor, the catalyst and the like used for the present invention can be replaced with others if they have the same functions as those used for the embodiments, provided that they do not disagree with the purpose of the present invention. For example, metal oxides such as $In_2O_3$, $SnO_2$, $Co_3O_4$, $NiO$, $CuO$ and $V_2O_5$, or composite oxides of these can be used for the ozone sensor. In addition, the structure of the apparatus can also be adapted in accordance with conditions corresponding to its capability and operation environment. The deterioration determination conditions are not limited to those of the embodiments, but the count number of detection intervals, which are shorter than the standard detection interval, can be increased for example.

Industrial Usability

Since deterioration of a catalyst for a deodorizing and disinfecting apparatus using ozone can be detected and determined with reliability in the present invention, it is possible to prevent discharge of excessive amounts of ozone to the outside the apparatus. Therefore, the deodorizing and disinfecting apparatus having the catalyst deterioration detection function of the present invention is expected to be used widely in many fields such as water treatment, medical and food industries.

We claim:

1. A deodorizing and disinfecting apparatus having a catalyst deterioration detection function comprising: an air supply portion for inhaling air; an ozone generating portion for discharging ozone to the inhaled air; a catalyst for accelerating the deodorizing and disinfecting actions and decomposition of said ozone, disposed downstream from said ozone generating portion; an ozone sensor for detecting the concentration of remaining ozone, disposed downstream from said catalyst; and means for repeating a cycle including stop of ozone discharge from said ozone generating portion for a predetermined time period when the concentration of said remaining ozone reaches a predetermined concentration or more, and for determining that said catalyst has been deteriorated when a condition wherein an interval between times when the concentration of said remaining ozone is not less than the predetermined concentration becomes shorter than a predetermined time interval is recognized at a predetermined frequency, and then for stopping discharge of said ozone.

2. The deodorizing and disinfecting apparatus having a catalyst deterioration detection function in accordance with claim 1, wherein said apparatus further comprising alarm means for notifying that said catalyst has been deteriorated when said catalyst is determined to be deteriorated and the ozone discharge is stopped.

3. A method of preventing discharge of excessive amounts of ozone from a deodorizing and disinfecting apparatus using ozone, comprising an ozone sensor, a signal processing unit, and an ozone generator, the method comprising the steps of:

a) stopping ozone generation in said ozone generator when the ozone sensor senses that the amount of ozone discharged from said deodorizing and disinfecting apparatus has reached an allowable limit;

b) resuming generation of ozone in said ozone generator after an elapsed time period;

c) stopping ozone generation in said ozone generator when the ozone sensor senses that the amount of ozone discharged from said deodorizing and disinfecting apparatus has reached the allowable limit again;

d) counting the number of times a detection interval is less than a standard detection interval, said detection interval being the amount of time between successive sensing operations in which the amount of ozone has reached the allowable limit;

e) stopping the operation of said deodorizing and disinfecting apparatus when said signal processing unit determines that the number of times that said detection interval is detected to be less than a standard detection interval is greater than a predetermined number.

4. The method of preventing discharge of excessive amounts of ozone from a deodorizing and disinfecting apparatus in claim 3, wherein step e) further comprises the step of generating an alarm when said signal processing unit determines that the number of times that said detection interval is detected to be less than a standard detection interval is greater than said predetermined number.

5. The method of preventing discharge of excessive amounts of ozone from a deodorizing and disinfecting apparatus in claim 3, wherein step e) further comprises the steps of:

counting the number of times said detection interval is detected to be less than a standard detection interval; and determining whether the counted number has reached said predetermined number.

6. The method of preventing discharge of excessive amounts of ozone from a deodorizing and disinfecting apparatus in claim 5, wherein said predetermined number is five.

7. The method of preventing discharge of excessive amounts of ozone from a deodorizing and disinfecting apparatus in claim 3, the deodorizing and disinfecting apparatus further comprising a catalyst for accelerating the deodorizing and disinfecting actions and the decomposition of said ozone, the method further comprising the step of:

determining the catalyst to be deteriorated when said signal processing unit determines that the number of times that said detection interval is detected to be less than a standard detection interval is greater than said predetermined number.

* * * * *